(12) United States Patent
Maxton et al.

(10) Patent No.: US 11,185,009 B2
(45) Date of Patent: Nov. 30, 2021

(54) SYSTEM AND METHOD FOR ON-THE-GO MEASUREMENTS OF TEMPERATURE AND DIELECTRIC PROPERTIES OF SOIL AND OTHER SEMI-SOLID MATERIALS

(71) Applicant: Veris Technologies, Inc., Salina, KS (US)

(72) Inventors: Chase Maxton, Salina, KS (US); Kyle Jensen, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 229 days.

(21) Appl. No.: 16/297,510

(22) Filed: Mar. 8, 2019

(65) Prior Publication Data

US 2019/0208698 A1      Jul. 11, 2019

Related U.S. Application Data

(60) Continuation-in-part of application No. 16/141,928, filed on Sep. 25, 2018, now Pat. No. 10,798,872, (Continued)

(51) Int. Cl.
*A01C 7/10*         (2006.01)
*A01C 7/20*         (2006.01)
(Continued)

(52) U.S. Cl.
CPC ............. *A01C 7/102* (2013.01); *A01B 49/04* (2013.01); *A01B 49/06* (2013.01); *A01B 63/008* (2013.01);
(Continued)

(58) Field of Classification Search
CPC .. A01C 7/102; A01C 7/10; A01C 7/08; A01C 7/00; A01C 5/06; A01C 5/00;
(Continued)

(56) References Cited

U.S. PATENT DOCUMENTS 3,084,553 A     4/1963 Cullinan et al.
3,224,512 A     12/1965 Alexander
(Continued)

OTHER PUBLICATIONS

Adamchuk et al., "On-the-go soil sensors for precision agriculture", Computers and Electronics in Agriculture, No. 44, pp. 71-91, Jun. 12, 2004.
(Continued)

*Primary Examiner* — Christopher J. Novosad
(74) *Attorney, Agent, or Firm* — Jeffrey L. Thompson; Thompson Law, P.A.

(57) ABSTRACT

A system for measuring temperature and dielectric properties of soil and other semi-solid materials on-the-go uses a long-wearing non-ferrous wear plate with two metal prongs supported by the wear plate to measure dielectric properties. The metal prongs each have a mounting end soldered to a printed circuit board containing a capacitance sensor circuit. The metal prongs have exposed ends arranged to contact the semi-solid material being measured. The sensor circuit has an oscillation frequency of 50 to 100 MHz to allow rapid dielectric measurements to be made as the sensor moves through the semi-solid material. In one embodiment, the system includes an implement for traversing a field, a shank with a leading edge for opening a furrow in soil, and a spring-loaded mounting system for biasing the wear plate downwardly relative to a shank to maintain a consistent pressure of the wear plate and metal prongs against the soil.

13 Claims, 10 Drawing Sheets

Related U.S. Application Data which is a continuation of application No. 15/452,404, filed on Mar. 7, 2017, now Pat. No. 10,080,323, which is a division of application No. 14/253,839, filed on Apr. 15, 2014, now Pat. No. 9,585,301.

(60) Provisional application No. 62/640,762, filed on Mar. 9, 2018, provisional application No. 61/812,131, filed on Apr. 15, 2013.

(51) Int. Cl.

| | | |
|---|---|---|
| *A01B 49/06* | (2006.01) | |
| *A01B 63/00* | (2006.01) | |
| *A01C 5/06* | (2006.01) | |
| *G01N 27/22* | (2006.01) | |
| *A01B 49/04* | (2006.01) | |
| *A01C 21/00* | (2006.01) | |
| *G01N 33/24* | (2006.01) | |
| *A01B 79/00* | (2006.01) | |
| *G01J 5/00* | (2006.01) | |
| *G01K 7/34* | (2006.01) | |
| *G01N 21/55* | (2014.01) | |
| *G01N 21/17* | (2006.01) | |

(52) U.S. Cl.
CPC ............ *A01B 79/005* (2013.01); *A01C 5/062* (2013.01); *A01C 5/064* (2013.01); *A01C 5/068* (2013.01); *A01C 7/203* (2013.01); *A01C 21/00* (2013.01); *G01J 5/00* (2013.01); *G01K 7/34* (2013.01); *G01N 27/223* (2013.01); *G01N 33/24* (2013.01); *A01C 5/06* (2013.01); *G01N 21/55* (2013.01); *G01N 2021/1738* (2013.01); *G01N 2033/245* (2013.01)

(58) Field of Classification Search
CPC ......... A01C 5/064; A01C 7/203; A01C 7/201; A01C 7/20; A01C 21/00; A01B 49/04; A01B 49/00; A01B 49/06; A01B 63/008; A01B 63/002; A01B 63/00; G01N 21/55; G01N 21/17; G01N 21/00; G01N 27/223; G01N 27/22; G01N 27/02; G01N 27/00; G01N 33/24; G01N 33/00; G01N 2021/1738; G01N 2023/245; G01J 5/00; G01K 7/34; G01K 7/00

See application file for complete search history.

(56) References Cited

U.S. PATENT DOCUMENTS

| | | | |
|---|---|---|---|
| 3,331,249 A | 7/1967 | Boxrud | |
| 3,464,504 A | 9/1969 | Stange | |
| 3,593,809 A | 7/1971 | Derry | |
| 3,625,296 A | 12/1971 | Mabry | |
| 3,774,237 A | 11/1973 | Hardway, Jr. | |
| 4,191,263 A | 3/1980 | Malterer | |
| 4,316,393 A | 2/1982 | Philipenko | |
| RE30,901 E | 4/1982 | Boxrud | |
| 4,332,301 A | 6/1982 | Jonell | |
| 4,333,541 A | 6/1982 | Doty | |
| 4,482,021 A | 11/1984 | Repski | |
| 4,531,087 A | 7/1985 | Larson | |
| 4,534,231 A | 8/1985 | Jonsson et al. | |
| 5,021,939 A | 6/1991 | Pulgiese | |
| 5,038,040 A | 8/1991 | Funk et al. | |
| 5,076,372 A | 12/1991 | Hellbusch | |
| 5,211,248 A | 5/1993 | Nosewicz et al. | |
| 5,394,949 A | 3/1995 | Wright et al. | |
| 5,435,399 A | 7/1995 | Peterson et al. | |
| 5,546,974 A * | 8/1996 | Bireley | A01G 25/167 137/78.3 |
| 5,741,983 A | 4/1998 | Skotnikov et al. | |
| 5,841,282 A | 11/1998 | Christy et al. | |
| 5,887,491 A | 3/1999 | Monson et al. | |
| 5,950,741 A | 9/1999 | Wright et al. | |
| 6,016,713 A | 1/2000 | Hale | |
| 6,116,172 A | 9/2000 | Prairie et al. | |
| 6,237,429 B1 | 5/2001 | Melnyk | |
| 6,260,633 B1 | 7/2001 | Machek et al. | |
| 6,360,829 B1 | 3/2002 | Naber et al. | |
| 6,363,803 B1 | 4/2002 | Hubers | |
| 6,592,820 B1 | 7/2003 | Hardman et al. | |
| 6,766,865 B1 | 7/2004 | Dagel et al. | |
| 6,959,245 B2 | 10/2005 | Rooney et al. | |
| 6,975,245 B1 | 12/2005 | Slater et al. | |
| 7,216,555 B2 | 5/2007 | Drummond et al. | |
| 7,255,016 B2 | 8/2007 | Burton | |
| 7,474,105 B2 * | 1/2009 | McDermid | G01N 27/223 324/664 |
| 7,552,654 B2 | 6/2009 | Burton | |
| 7,827,873 B2 | 11/2010 | Burton | |
| 8,451,449 B2 | 5/2013 | Holland | |
| 8,573,074 B1 | 11/2013 | Marker | |
| 9,585,301 B1 | 3/2017 | Lund et al. | |
| 9,651,536 B1 | 5/2017 | Lund et al. | |
| 9,743,574 B1 | 8/2017 | Maxton et al. | |
| 10,080,323 B2 * | 9/2018 | Lund | A01B 63/008 |
| 10,321,623 B1 | 6/2019 | Maxton et al. | |
| 10,798,872 B1 * | 10/2020 | Lund | A01B 49/06 |
| 2002/0131046 A1 | 9/2002 | Christy et al. | |
| 2003/0016029 A1 | 1/2003 | Schuler et al. | |
| 2004/0052686 A1 | 3/2004 | Hardman et al. | |
| 2005/0034437 A1 | 2/2005 | McMurtry et al. | |
| 2005/0172733 A1 | 8/2005 | Drummond et al. | |
| 2005/0279163 A1 | 12/2005 | Chesk | |
| 2006/0114006 A1 | 6/2006 | Mohamed | |
| 2007/0068238 A1 | 3/2007 | Wendte | |
| 2007/0151467 A1 | 7/2007 | Furll et al. | |
| 2008/0199359 A1 | 8/2008 | Davis et al. | |
| 2010/0222750 A1 * | 9/2010 | Cheng | A61B 17/864 604/288.04 |
| 2010/0275565 A1 | 11/2010 | Moe et al. | |
| 2011/0102798 A1 * | 5/2011 | Holland | G01N 21/31 356/445 |
| 2011/0106451 A1 | 5/2011 | Christy et al. | |
| 2011/0203356 A1 | 8/2011 | Scherbring | |
| 2012/0048160 A1 | 3/2012 | Adams et al. | |
| 2012/0089304 A1 | 4/2012 | Hamilton et al. | |
| 2012/0091222 A1 | 4/2012 | Dresselhaus et al. | |
| 2012/0130552 A1 | 5/2012 | Schmidt et al. | |
| 2012/0297895 A1 * | 11/2012 | Kapas | G01L 3/102 73/862.193 |
| 2013/0046446 A1 | 2/2013 | Anderson | |
| 2013/0191073 A1 | 7/2013 | Rice et al. | |
| 2013/0250305 A1 | 9/2013 | Holland | |
| 2013/0325267 A1 | 12/2013 | Adams et al. | |
| 2014/0116735 A1 | 5/2014 | Bassett | |
| 2014/0303854 A1 * | 10/2014 | Zielke | G01K 1/14 701/50 |

OTHER PUBLICATIONS

Fares et al., "Improved Calibration Functions of Three Capacitance Probes for the Measurement of Soil Moisture in Tropical Soils", Sensors, No. 11, pp. 4858-4874, May 3, 2011.

* cited by examiner

SYSTEM AND METHOD FOR ON-THE-GO MEASUREMENTS OF TEMPERATURE AND DIELECTRIC PROPERTIES OF SOIL AND OTHER SEMI-SOLID MATERIALS

RELATED APPLICATIONS

This application claims the benefit of U.S. Provisional Patent Application No. 62/640,762 filed on Mar. 9, 2018. This application is also a continuation-in-part of U.S. patent application Ser. No. 16/141,928 filed on Sep. 25, 2018, which was a continuation of U.S. patent application Ser. No. 15/452,404 filed on Mar. 7, 2017, now U.S. Pat. No. 10,080,323, which was a divisional of Ser. No. 14/253,839 filed on Apr. 15, 2014, now U.S. Pat. No. 9,585,301, which claims the benefit of U.S. Provisional Patent Application No. 61/812,131 filed on Apr. 15, 2013. The entire contents of these prior applications are incorporated herein by reference.

BACKGROUND OF THE INVENTION

Field of the Invention

The present invention relates generally to systems and methods for measuring properties of soils and other semi-solid materials, and in particular, to systems and methods for measuring temperature and dielectric properties of soil and other semi-solid materials on-the-go.

Description of the Related Art

Soils typically contain about 25% air, which allows proper water infiltration, root growth, and microbial activity. If soils are mechanically cultivated when they are too wet, the soil structure can be damaged, reducing the pore space which leads to water and nutrient run-off, reduced soil health, and reduced crop yields. Soil moisture varies within fields in the XY axis and in the –Z axis due to soil texture, organic matter, landscape position, crop residue on the surface, previous tillage effects, and other factors. Farmers typically set their tillage tools to achieve the task at hand, which can be weed removal, seedbed preparation, soil drying, and levelling of previous tillage effects. Farmers don't intentionally damage their soil, but they are often not fully aware of potentially harmful soil moisture conditions at certain depths and in certain locations in their fields.

For seeds to germinate and transplanted seedlings to achieve optimal growth, they must be planted in an optimal soil environment. For example, corn requires a minimum soil temperature of 50° F. to germinate, and studies have shown steadily increasing germination and shoot development in soil temperatures up to 80° F. A minimum amount of soil moisture is required as well; corn absorbs a minimum moisture amount of 30% of its seed weight to germinate. Studies have shown that corn seed must be planted at a 1.5-2.5" depth for optimal germination, emergence, and crown root development. In early spring conditions, soil temperatures can vary significantly within that optimal range with warmer temperatures at shallow depths, especially as crop residue, soil texture, organic matter and other factors including landscape position vary within a field. If temperatures are below 50° at the current planting depth, adjusting the planter to a shallower setting would be required for seeds to be placed in >50° soils. In drier regions, soil moisture may vary widely within the optimal seeding depth range, with the need to plant deep for the seed to have adequate moisture for germination. As a farmer makes planting date decisions and planter adjustments, he must evaluate soil moisture and temperature to insure his seeds are placed in the optimal combination of warm and moist soil. Typically, a farmer is only able to take a small number of soil temperature readings in a field, even though his fields have dozens and perhaps hundreds of micro-environments that cause wide swings in soil temperature. Likewise, his moisture investigations are sparse and in most cases qualitative rather than quantitative as growers typically rely on a simple feeling or squeezing of soil to assess moisture levels.

To schedule irrigation applications and to apply the proper amount of water at each application, growers and their consultants measure soil moisture. The state-of-the-art practice is to place fixed soil moisture probes in the field, typically at only one or two locations due to expense and the complicated installation procedure. Yet there are many soil moisture variations within the irrigated area due to soil texture, topsoil depth, organic matter, landscape position, as well as moisture usage by the irrigated crop and localized rainfall variations.

Soil mapping using on-the-go sensors is already a well-accepted practice. The primary on-the-go sensors that have been commercialized and the soil properties they relate to are: soil electrical conductivity (EC) sensors which relate to soil texture and salinity, soil optical reflectance sensors which relate to organic matter (OM), and LIDAR and GPS sensing of topography including slope, aspect, and curvature. Additionally, there are fixed location sensors such as penetrometers which measure soil compaction; while not commercialized there are also on-the-go sensors that relate to compaction. For each of these sensors and their properties, varying levels of soil moisture creates complex interactions. For example, EC levels rise with soil moisture and with higher temperatures, optical soil reflectance diminishes with soil moisture, and soil moisture is likely higher in concave landscape positions. Soil's radiation emissivity factor that temperature sensors detect can be affected by soil color, which is largely determined by organic matter levels.

Accurately measuring the dry bulk density of soils is especially important for precise measurements of soil organic carbon. For the purpose of assessing soil carbon change, which is relevant for greenhouse gas and climate change initiatives, baseline and subsequent measurements are needed at the landscape, field and even region or country scale. The change in soil carbon is typically quite small, and differences in bulk density can thwart the carbon change evaluation process. Efforts to use on-the-go soil sensors including optical sensing have been limited by their inability to deal with the variations in bulk density that moisture differences create.

Soil penetration resistance measurements, commonly referred to as compaction, are soil measurements that have significant potential to improve crop production, but have not been widely adopted due to confounding and unaccounted for levels of soil moisture. Soil penetration resistance is higher when soils are dry, leading to the question— is the resistance due to compaction or dry soil?

There is a need for a system and method for on-the-go sensing of soil moisture and soil temperature, and for using those measurements to improve various processes, such as tillage, planting, soil mapping, irrigation scheduling, and various other processes.

BRIEF DESCRIPTION OF THE DRAWINGS

The present invention will become more clearly appreciated as the disclosure of the present invention is made with reference to the accompanying drawings. In the drawings:

FIGS. 3, 4 and 5 are side elevation views of various operating positions of a sensor module for measuring soil moisture and soil temperature; FIG. 3 shows the sensor module in a lower position (e.g., when operating in light, sandy soils or when the implement is raised out of the ground); FIG. 4 shows the sensor module in a normal operating position with down pressure being applied by the internal spring; and FIG. 5 shows the sensor module in a raised position (e.g., when engaging a rock or other obstacle in the soil).

DETAILED DESCRIPTION OF THE INVENTION

A method and system for measuring soil moisture and soil temperature and other soil properties according to the present invention will now be described in detail with reference to FIGS. 1 to 12 of the accompanying drawings.

A sensor assembly 10 used in the present invention includes a capacitance sensor 11 for measuring soil moisture (or other properties related to the dielectric constant of a material), and a thermopile temperature sensor 12 for measuring soil temperature at the same depth as the soil moisture measurement. These two sensor technologies are explained below.

Capacitance Sensor

The present invention uses a capacitance sensor 11 to measure the dielectric or permittivity of a material—that is the ability of a material to store electrical energy. The amount of energy stored relates to the composition of the material. Soil is comprised of Air (dielectric constant=1), minerals (dielectric constant ranges 3 to 8), and water (dielectric constant=80). Because the dielectric constant of water is much higher than that of minerals typically found in soil, or that of air, a sensor which detects the permittivity of the soil would be mostly influenced by the soil moisture. However, some care needs to be taken to be sure a consistent density of soil is maintained. Because the dielectric of air is much lower than water, any extra air that's introduced into the soil or measured material can induce errors. Having a consistent pressure applied to the sensor allows for a more stable density and less air gaps, which in turn reduces measurement error.

The capacitance sensor 11 used in the present invention uses a high oscillation frequency. For example, the oscillation frequency can be in the range of 50 to 150 MHz, or approximately 100 MHz. This high oscillation frequency reduces the effects of soil texture and salinity. This frequency is applied to the measured material, and the time it takes the material to reach the charge is measured; which correlates to the material's dielectric properties. This is all done very rapidly—in a matter of a couple microseconds; which allows for rapid dielectric measurements to be made as the sensor is moving through the soil or measured material. The soil's dielectric measurement can then be converted to a moisture % using a multitude of dielectric to soil moisture calculations. Alternatively, this dielectric sensor could detect other properties besides moisture in a multitude of materials. For example, vinegar has a dielectric of 24, and is a component of various foods. A calibration curve could be developed to detect % vinegar in food production.

Soil Temperature Sensor

The present invention uses a thermopile temperature sensor 12 to detect the IR radiation released by an object. The intensity of the IR radiation relates to the object's temperature. The IR radiation occurs at the speed of light—therefore this measurement can be taken very quickly. IR radiation can only be measured on the surface of an object. The IR temperature sensor used in the present invention is in direct contact with the soil or other semi-solid material, so there's no ambiguity about where the IR radiation is coming from.

Implement Row Unit

Figure 1:
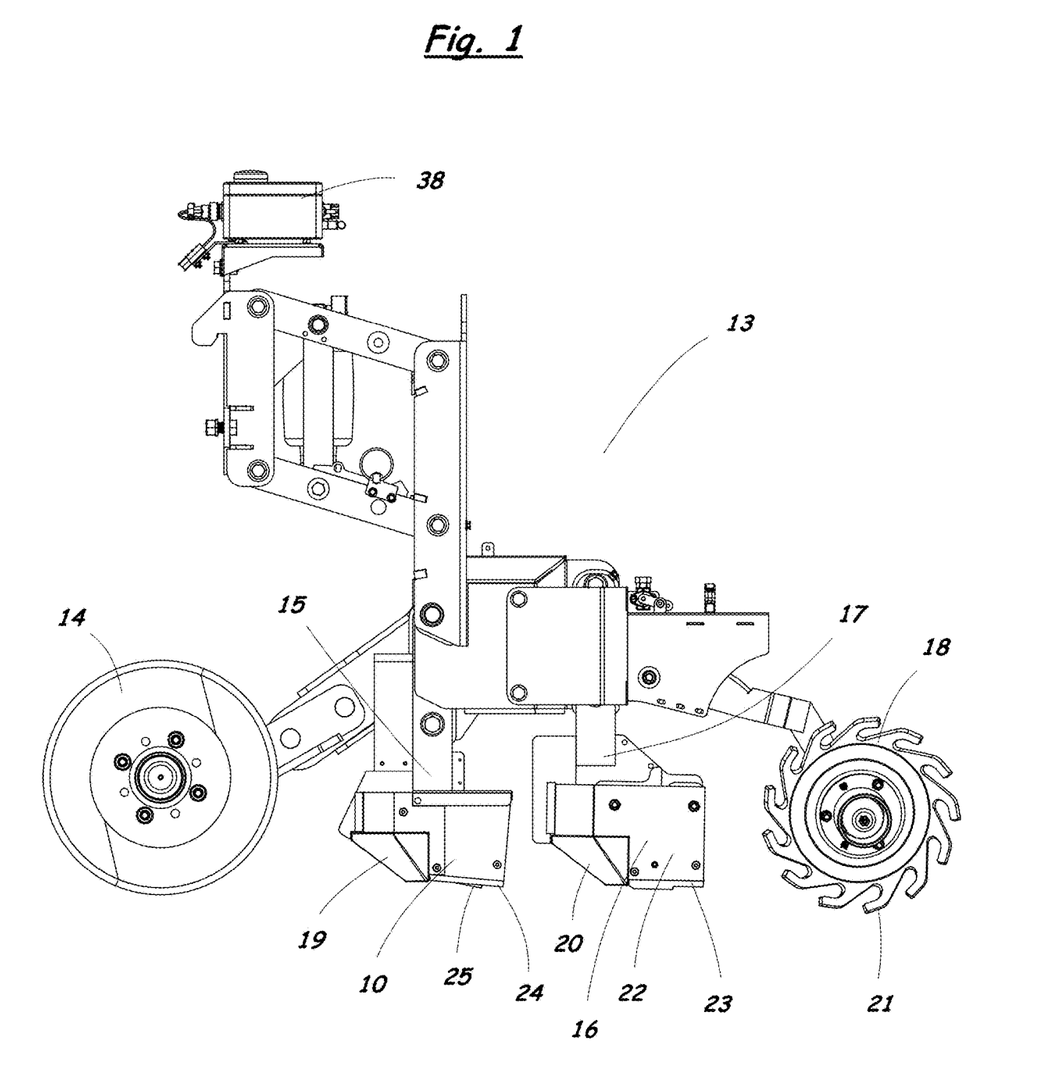
FIG. 1 is a side elevation view of a sensor row unit equipped with a system for measuring multiple soil properties according to the present invention.
Figure 2:
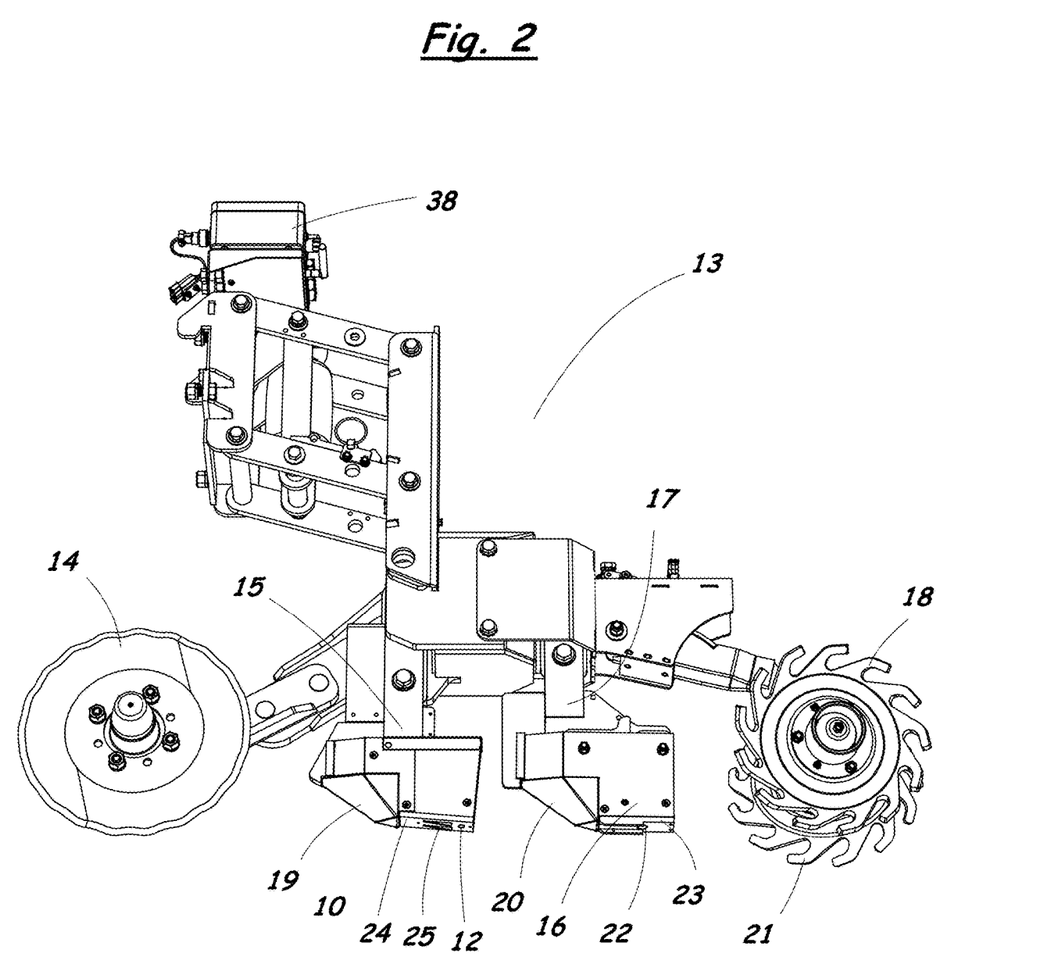
FIG. 2 is a bottom perspective view of the sensor row unit shown in FIG. 1.
Figure 3:
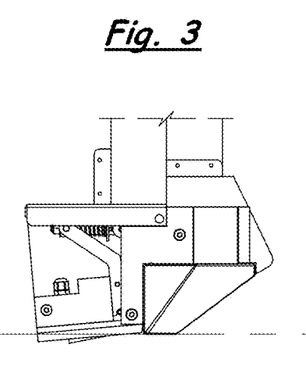
Figure 4:
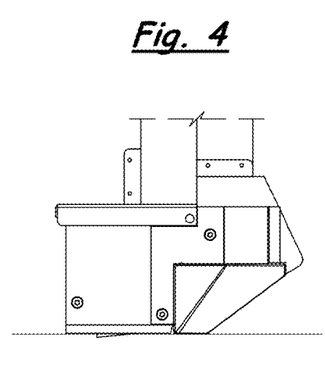
Figure 5:
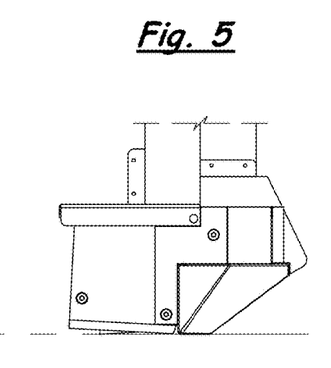

FIGS. 1 and 2 illustrate a sensor row unit 13 for measuring multiple soil properties according to the present invention. The row unit 13 includes a front coulter 14 for cutting through residue and for opening a slot in the soil, the first sensor assembly 10 mounted to a first shank 15 for measuring soil moisture and soil temperature, a second sensor assembly 16 mounted to a second shank 17 for measuring soil optical properties, and a furrow closing assembly 18 that follows along behind the second sensor assembly 16 to close the furrow. A leading carbide edge 19 is attached to the lower end of the first shank 15, and a leading carbide edge 20 is attached to the lower end of the second shank 17.

A soil EC measuring system is also provided in the sensor row unit 13. The soil EC measuring system uses four soil engaging components as electrodes to measure soil EC. The front coulter 14 serves as a first electrode; the leading carbide edge 19 at the lower end of the first shank 15 serves as the second electrode; the leading carbide edge 20 at the lower end of the second shank 17 serves as the third electrode; and the teeth 21 on the furrow closing assembly 18 serve as the fourth electrode. The four soil engaging components 14, 19, 20, 21 serving as electrodes are conductive metal, and are each electrically isolated from the rest of the sensor row unit 13 by a nonconductive mounting system.

The second sensor assembly 16 includes an optical module 22 with a hardened wear plate 23 on its bottom surface. The hardened wear plate 23 presses against the soil within the furrow during operation. The wear plate 23 contains a sapphire window and a photodiode for obtaining soil reflectance measurements. The optical module 22 can have the same structure and function as the optical module described in the Applicant's U.S. Pat. No. 9,651,536 issued on May 16, 2017, for an invention titled "Method and System for Measuring Multiple Soil Properties."

The first sensor assembly 10 for measuring soil moisture and soil temperature is mounted at the lower end of the first shank 15 behind the leading carbide edge 19. The first sensor assembly 10 includes a non-ferrous wear plate 24 mounted to the shank 15 behind the leading edge 19. The wear plate 24 can be formed of a long-wearing non-ferrous material, such as ceramic impregnated ultra high molecular weight (UHMW) polyethylene or crosslink UHMW polyethylene.

Figure 6:
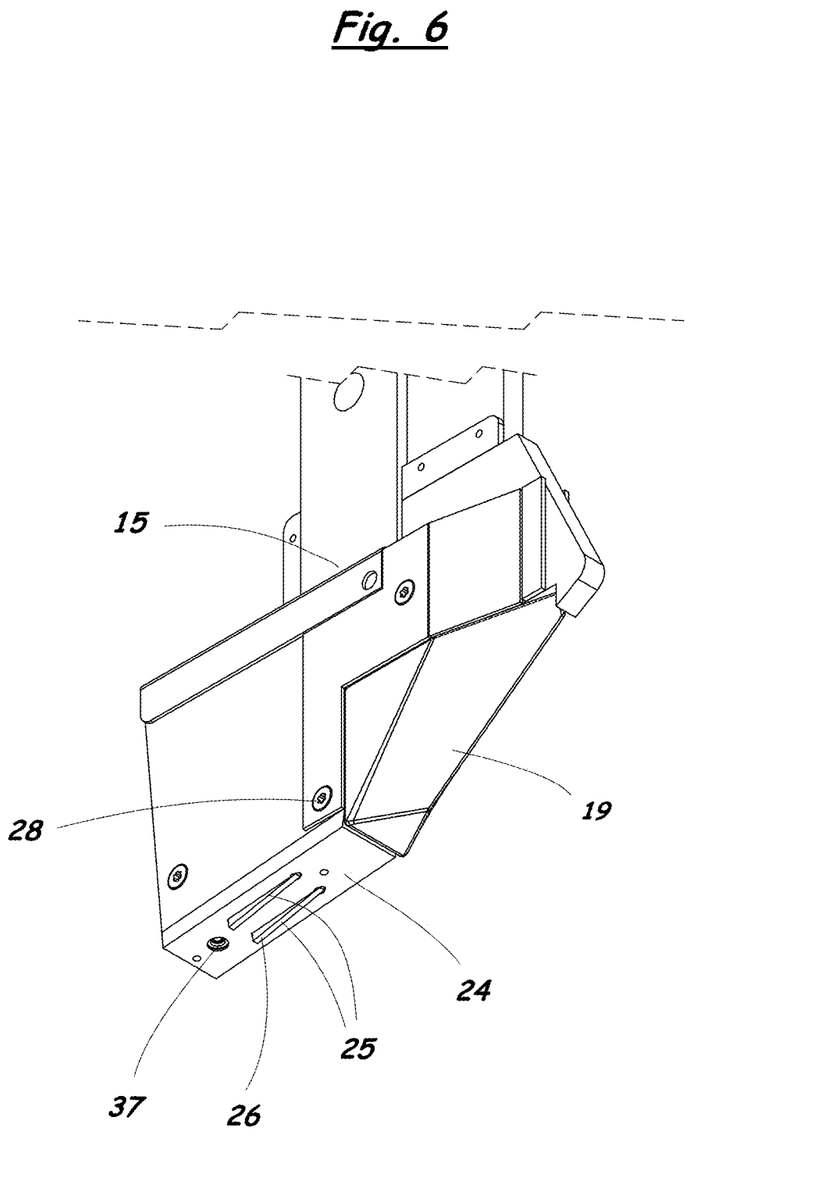
FIG. 6 is a bottom perspective view of the sensor module for measuring soil moisture and soil temperature.

Two metal prongs 25 are embedded in the wear plate 24 and have exposed lower ends 26 arranged to contact soil in a bottom of the furrow created by the leading carbide edge 19. The two metal prongs 25 are spaced apart and isolated from each other by the wear plate 24. The lower portions 26 of the metal prongs 25 are sloped downwardly and rearwardly to provide a sloped soil-engaging surface that rides over rocks and other objects in the soil.

Figure 7:
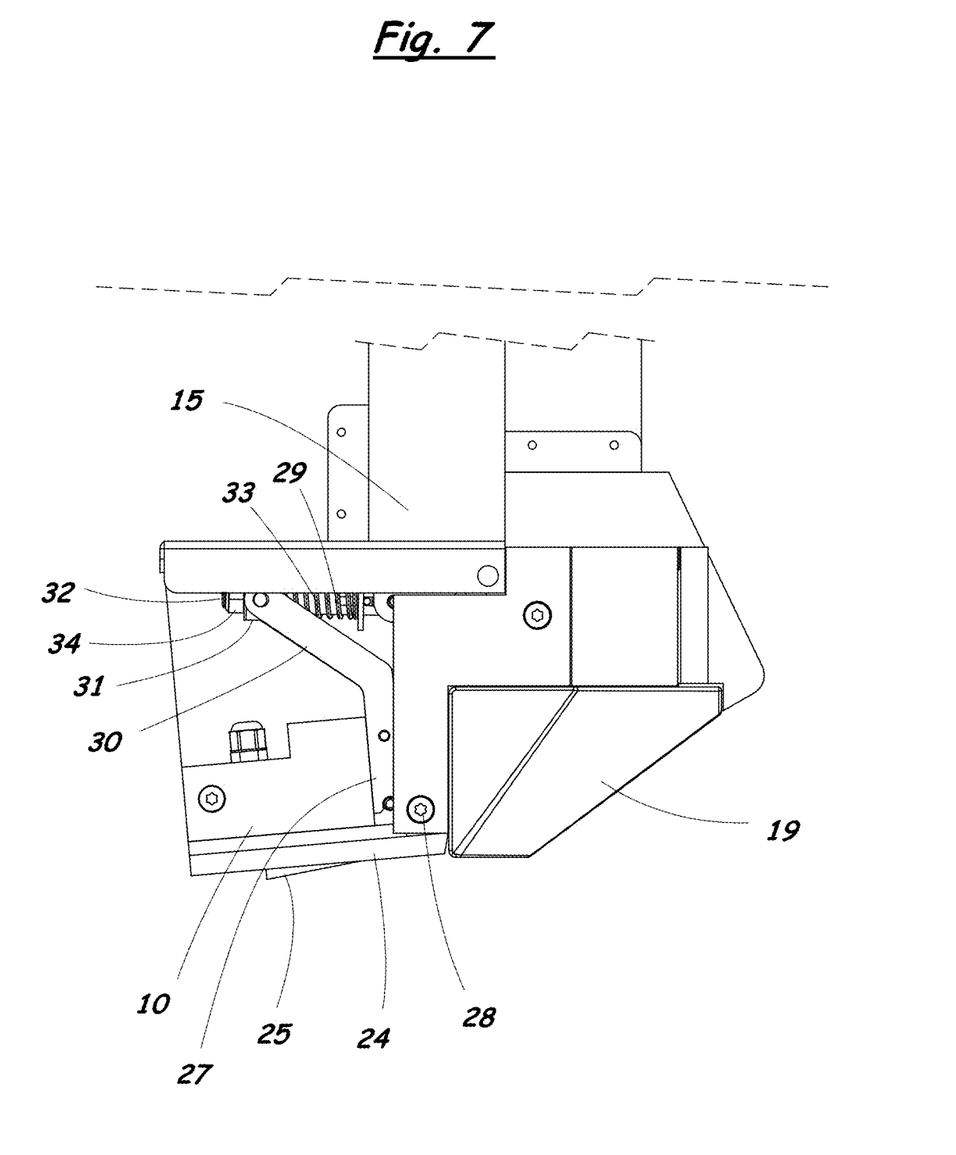
FIG. 7 is a cutaway side view of the sensor module shown in FIG. 6.

As illustrated in FIG. 7, a spring-loaded mounting system 27 is provided for mounting the first sensor assembly to the lower end of the first shank 15. The mounting system 27 functions to bias the wear plate 24 downwardly relative to the first shank 15 to maintain a consistent pressure of the wear plate 24 and metal prongs 25 against the soil. The mounting system 27 includes a pivot connection 28 between the front portion of the first sensor assembly 10 and the lower end of the first shank 15 behind the leading carbide edge 19. A spring assembly 29 is arranged to bias the wear plate 24 to rotate about the pivot connection 28 in a direction that causes a rear portion of the wear plate 24 to press downwardly against the soil.

A support arm 30 of the mounting system 27 has a lower portion fixed to a front portion of the first sensor assembly 10, and an upper end pivotally connected to a bushing 31 on the spring assembly 29. The spring assembly 29 includes a threaded bolt 32, a compression spring 33 installed on the bolt 32, the bushing 31 to which the support arm 30 is attached, and a threaded nut 34. The threaded nut 34 provides a stop limit for limiting the downward rotation of the wear plate 24 relative to the shank 15.

Figure 8:
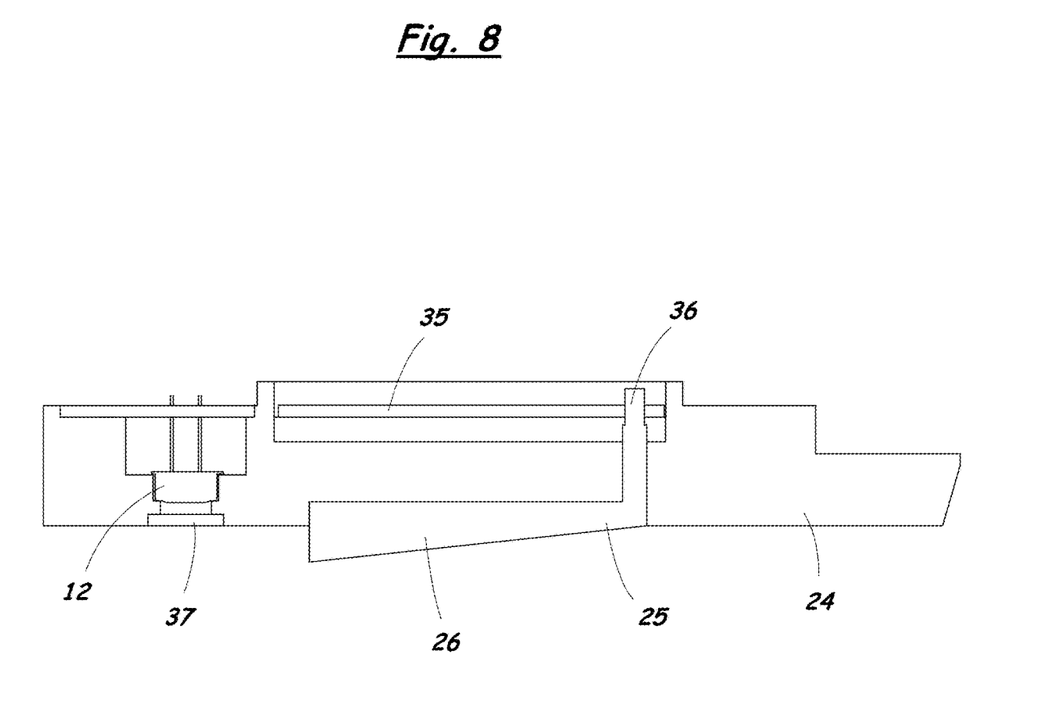
FIG. 8 is a cross section side view of a portion of the sensor module including a wear plate, moisture prong, printed circuit board, and temperature sensor.

As illustrated in FIG. 8, a printed circuit board 35 is mounted on an upper side of the non-ferrous wear plate 24. A capacitance sensor circuit is provided on the printed circuit board 35. The sensor circuit has an oscillation frequency of 50 to 150 MHz to allow rapid dielectric measurements to be made as the sensor assembly 10 moves through the soil or other semi-solid material. For example, an oscillation frequency of approximately 100 MHz in the sensor circuit on the printed circuit board 35 has been used with good results.

The metal prongs 25 each have an upper mounting end 36 soldered directly to the printed circuit board 35. By soldering the metal prongs 25 directly to the printed circuit board 35, the present invention reduces the interconnect capacitance that would otherwise interfere with the dielectric measurements by the capacitance circuit. The high frequency oscillations of the capacitance circuit would cause any such wires and connectors to become inductors with capacitance, which would interfere with the dielectric measurements of the soil or other semi-solid material being measured.

The soil temperature sensing device 12 is mounted to the wear plate 24 behind the metal prongs 25 (as illustrated in FIGS. 6 and 8), or between the metal prongs 25. A silicon window 37 is embedded in the wear plate 24 to allow IR radiation from the soil at the bottom of the furrow to reach the temperature sensing device 12. The metal prongs 25 help protect the silicon window 37 during use, especially with the window 37 positioned in the wear plate 24 between the metal prongs 25.

Data from the dielectric measurements and the temperature measurements, as well as the soil optical and soil EC measurements, can be georeferenced using a GPS signal from a GPS receiver connected to a DataLogger or PC 38 on the implement.

The system for on-the-go measurements of temperature and dielectric properties according to the present invention can be used in various applications, including agricultural applications relating to soil conditions (e.g., tillage and seedbed preparation, planting, irrigation and soil mapping), agricultural applications relating to harvested materials (e.g., hay and cotton), and other agricultural and industrial applications. Some of these applications will be discussed in further detail below.

Agricultural Applications—Tillage and Seedbed Preparation:

A soil-engaging moisture and temperature sensor mounted to the tillage tool would provide precise, geo-referenced, and quantitative information about the soil moisture levels throughout their field. Armed with this information, the farmer would be able to make better tillage decisions and adjustments, including utilizing real-time depth control available on some tillage implements today. Such information, including soil temperature acquired during the seedbed preparation pass immediately ahead of planting, could inform planting decisions as well.

Agricultural Applications—Planting:

A moisture and temperature sensor mounted to the planter would provide precise, geo-referenced and spatially dense information about the soil moisture and temperature within a farmer's seedbeds, enabling fact-based and accurate planting decisions and adjustments. This could lead to these adjustments being made in real-time and even automatically as planter technology adapts and is able to incorporate soil temperature and moisture data.

Agricultural Applications—Irrigation:

A mobilized soil moisture sensor, perhaps attached to the irrigation pivot wheel structure or attached to a field robot, could provide real-time, spatially dense soil moisture information immediately ahead of an irrigation application to guide optimal applications of water.

Agricultural Applications—Soil Mapping:

Adding precise soil moisture and temperature readings to the currently available soil sensors would provide the opportunity to remove the confounding effects of temperature and moisture. This would improve soil property mapping within a field and allow sensor data to be better utilized in its native form, even without lab sample validation. Likewise, each soil sensor measurement could be used to improve the accuracy of on-the-go temperature and moisture measurements. Soil's radiation emissivity factor that temperature sensors detect can be affected by soil color, which is largely determined by organic matter levels. The dielectric constant which is used for moisture measurement can be affected by soil texture and temperature. A suite of EC, optical, capacitance, and temperature sensors provides the opportunity to create proprietary calibrations using previously unmeasured and confounding factors. Co-located and simultaneous measurements of these sensors and statistical analyses of each would lead to improved soil property estimations.

Other Agricultural and Industrial Applications:

Precise soil moisture measurements will improve the bulk density estimations and allow more precise and spatially dense soil carbon measurements.

Accurately measuring soil moisture would clarify whether soil penetration resistance is due to compaction or dry soil, and wider adoption of soil resistance measurements would lead to site-specific alleviation of compaction as a yield-limiting factor.

Soil is not the only material that would benefit from on-the-go temperature and moisture sensing. For example, high temperature and moisture levels in hay can lead to spoilage and even spontaneous combustion. A moisture and temperature sensor mounted to a hay baler within the bale chamber could be used to monitor the bales as they are created and moved through the baler. In that case the sensor is fixed and the measured material is moving. Similarly, cotton harvesting decisions would benefit from improved moisture and temperature measurements using a fixed sensor that cotton moves against during the baling and module building process.

A successful composting process requires closely monitoring temperatures and moisture levels of the material, to have adequate temperatures for killing pathogens but at temperatures and moisture levels that promote the composting process. A temperature and moisture sensor mounted to a compost turner would provide geo-referenced measurements within the compost pile or windrow as it is being turned. These could be used to monitor the overall process and identify potential problem areas within the composting material.

Because each liquid and semi-liquid media has a unique dielectric constant, sensors that measure the dielectric constant can be used for monitoring. Areas that are large enough to have spatial variability and micro-environments, such as manure lagoons, water-treatment plants, and manmade fish ponds as well as natural bodies of water would benefit from the spatially-dense capability of geo-referenced on-the-go dielectric and temperature measurements.

An on-the-go dielectric and temperature sensor could be mounted on a probe, collecting a profile lithology of moisture, temperature, and other materials with unique dielectric constants. For environmental contamination investigations, materials of interest such as volatile organic compounds, have unique dielectric constants that could be detected with a dielectric probe.

The system for measuring soil properties on-the-go described herein has other features and benefits, as described below:

Temperature and moisture measurements are made at a precise depth, and depth is adjustable. This allows measurements to be acquired at the depth that will be most informative, for example above, below or at a tillage or planting depth.

Small and precisely determined soil volume is measured to provide information on soil moisture and temperature at a specific area of investigation which is known and controlled.

Mounting of soil prongs directly to the capacitance circuit reduces any effects of capacitance from signal wires.

Sensor prong is AC coupled to the measured material via a series capacitor. This eliminates excessive capacitance loading on the circuit, which produces a more stable and predictable sensor response.

Temperature is sensed via a thermopile through an optical window capable of transmitting in the infrared range from 1.2-7 um.

Temperature sensor's emissivity factor can be adjusted by co-located soil color measurements.

Dielectric sensor calibration can be compensated by co-located soil temperature measurements.

Co-located soil EC and organic matter measurements can be used to develop soil specific dielectric to moisture calibrations.

PCB and prongs are mounted in a fashion to dampen shock impact.

Effects of air are minimized by the prong and housing design—both work together to ensure complete soil contact and consistent air % is present in the soil.

Mounting can be on planter, tillage tool, seed firmer, irrigation pivot, or other mobile agriculture implements.

Advantages Over Existing Devices:

There have been a few attempts by university researchers to develop on-the-go capacitance sensing. (references— Whelan 2008, Adamchuk/Dillon 2010). Whelan's was a set of capacitance probe rings mounted horizontally, and the Dillon/Adamchuk device had electrodes on the side of a shank, where soil firmness would be inconsistent. These have utilized capacitance electrodes in a configuration that did not maintain adequate consistent soil contact, allowing variations in the soil/air ratio to confound the readings. None were commercialized.

Commercialized Technology:

Fixed Sensors—Capacitance Probes, Time Domain Reflectometry (TDR), Neutron Probes, Gypsum Blocks, Thermocouple and Other Temperature Sensors:

Fixed location moisture and temperature sensors only measure at a few locations that can be manually tested. Research has shown that soil moisture varies widely within fields. The present invention provides dense geo-referenced measurements for mapping and analysis. A serious limitation to capacitance moisture probes, which have become the ag industry standard, is the introduction of air into the measurement as soil adjacent to the capacitance electrodes dries and shrinks. As a result, there is typically a time-consuming probe installation process required to create a soil slurry around the capacitance probe as an attempt to minimize the error caused by irregularities in the dielectric constants. In contrast, the present invention is mobile and keeps air-induced error at a minimum due to its unique design of applying consistent pressure on the electrodes and the soil they are contacting.

Mobile Sensors

Ground-penetrating radar (GPR) is only suitable for use in sandy or relatively coarse-textured soils, the images require detailed analysis and post calibration to relate to moisture, and it measures a general and unknown volume of soil.

Microwave, hyperspectral, and thermal imaging signals respond to multiple unknown interactions of soil and vegetation properties; soil measurements are only viable in bare soil with no vegetation, and even then imagery requires detailed analysis and post calibration with frequent weak correlations to measured moisture; such imaging measures a general and unknown volume of soil.

Soil electrical conductivity EC measurements are relative readings depending on soil texture, moisture, salinity temperature, and density. EC data is collected from a volume of soil that can be approximated but not known specifically. Because of the complex and difficult to isolate factors which affect soil EC measurements, they have not been found to be a reliable moisture sensor, according to the bulk of published research.

Soil optical measurements are relative readings depending on sensor window condition, organic matter, soil moisture, and soil color. Because of the complex and difficult to isolate factors which affect soil optical measurements, they have not been found to be a reliable moisture sensor, according to the bulk of published research. If optical measurements are collected with a planter row unit device such as one mounted to a seed firmer, the reading can only be taken at the depth the planter is planting. The grower needs to know what conditions are above and below the current planting depth so as he evaluates changing his planter settings he knows what his options are. If the objective of using a planter-mounted optical window and temperature sensor is to monitor the soil condition where the seed is deposited, the window must be seeing the very bottom of the furrow, not the furrow side. Not only is the present invention an actual moisture sensor rather than simple optical sensor, it is seeing the bottom of the furrow it creates, and the operating depth is adjustable. This provides the grower with the soil moisture and temperature information he needs for optimal planting.

OTHER EMBODIMENTS

Multiple excitation frequencies could be measured with the same device. Sweeping through several frequencies could help ascertain other soil properties which respond at different sensor frequencies.

Figure 9:
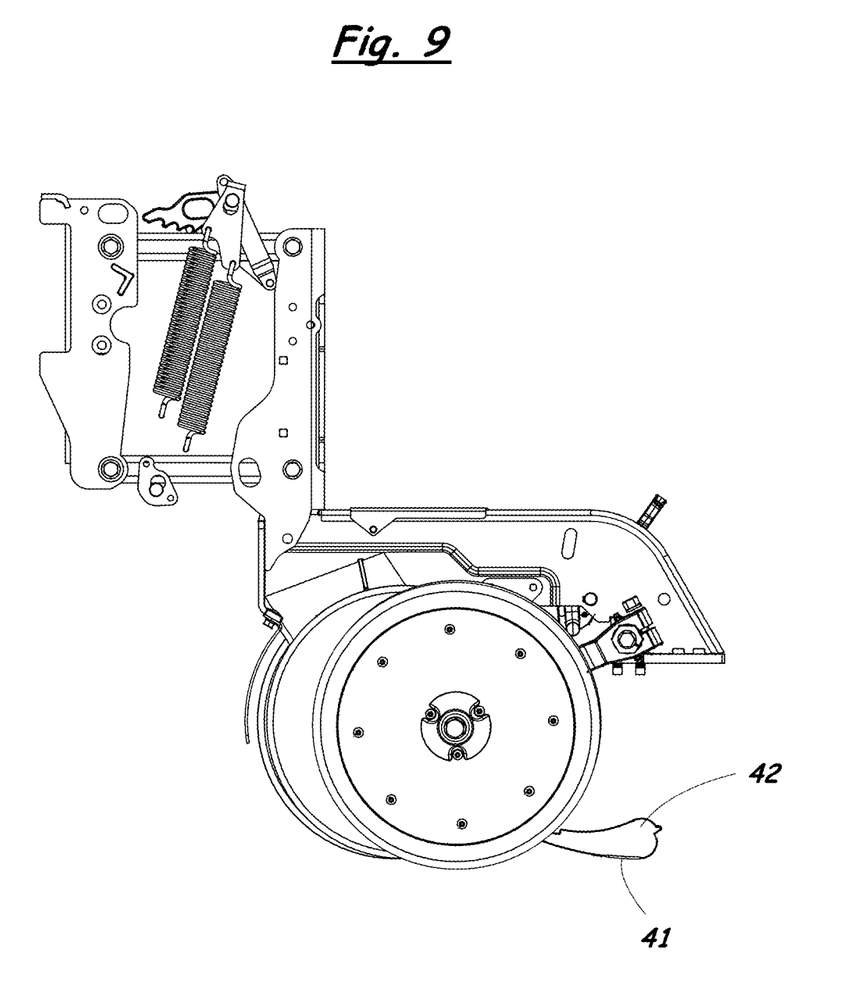
FIG. 9 is a side elevation view of a planter row unit with a sensor module for measuring soil moisture and soil temperature incorporated into a seed firmer.
Figure 10:
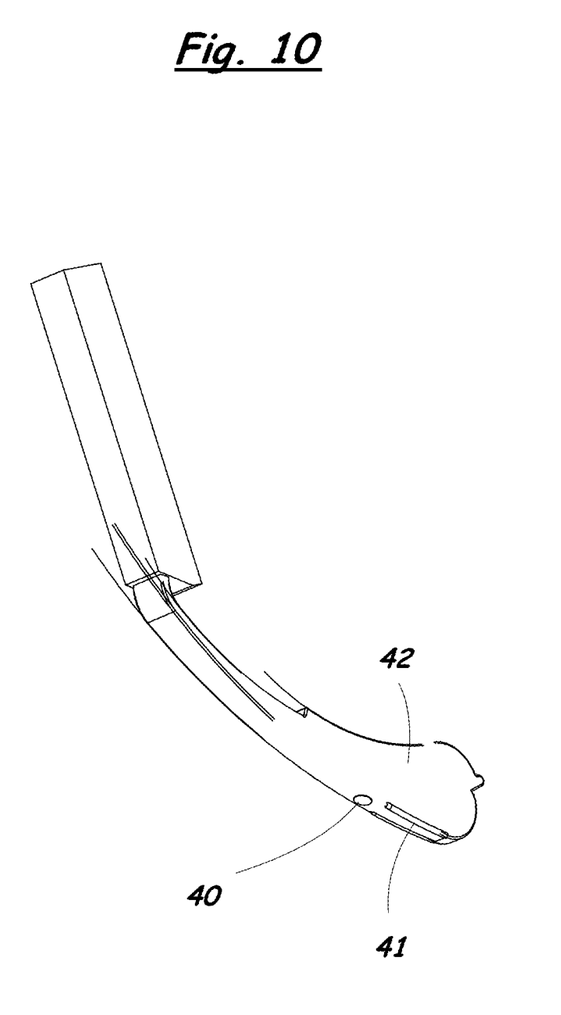
FIG. 10 is a perspective bottom view of the seed firmer shown in FIG. 9.

A capacitance sensor 40 and a temperature sensor 41 could be mounted on the bottom of a seed firmer 42, as illustrated in FIGS. 9 and 10.

Figure 11:
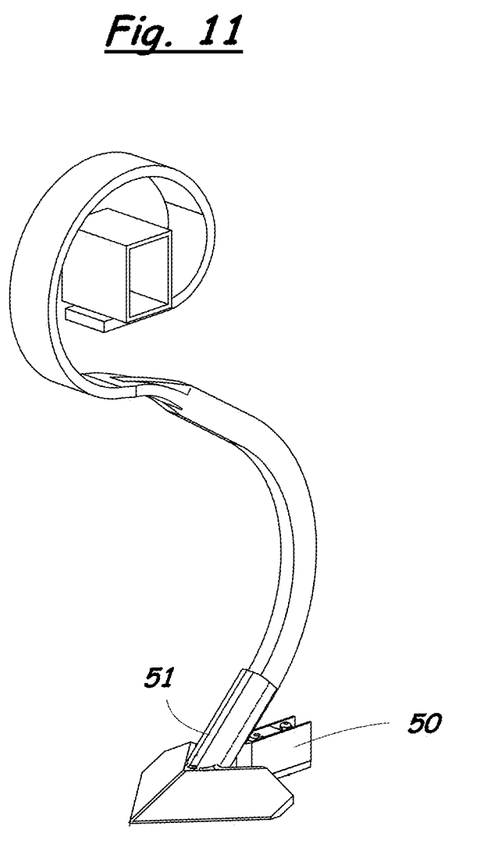
FIG. 11 is a perspective view of a tillage sweep with a sensor module mounted behind the sweep for measuring soil moisture and soil temperature.

A capacitance sensor and a temperature sensor could be incorporated into a sensor module 50 mounted on a tillage sweep 51, as illustrated in FIG. 11.

Figure 12:
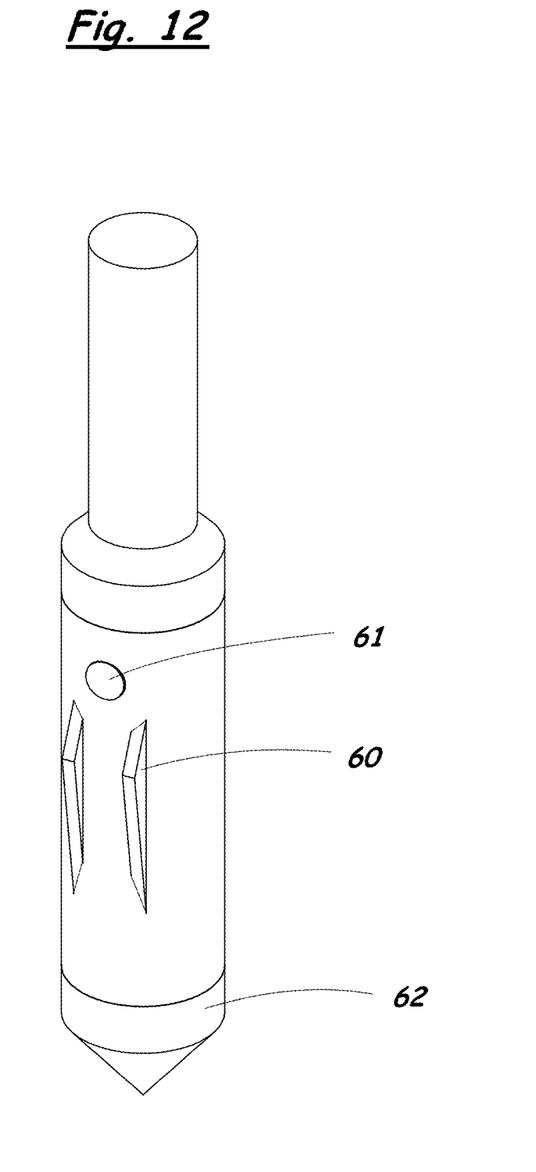
FIG. 12 is a perspective view of a probe for measuring soil moisture and soil temperature throughout a rooting zone.

A capacitance sensor 60 and a temperature sensor 61 could be mounted on a probe 62, as illustrated in FIG. 12, to measure soil moisture, dielectric and temperature throughout the rooting zone.

A capacitance sensor can be attached to a mobile irrigation system to monitor soil moisture while irrigating.

While the invention has been described in connection with specific embodiments thereof, it is to be understood that this is by way of illustration and not of limitation, and the scope of the appended claims should be construed as broadly as the prior art will permit.

What is claimed is:

1. A system for measuring soil moisture on-the-go, comprising:
    a non-ferrous wear plate arranged to contact soil during operation; and
    two metal prongs that are supported by said wear plate, said two metal prongs being electrically isolated from each other by said wear plate and arranged to contact soil to measure dielectric properties of the soil.

2. The system according to claim 1, wherein said non-ferrous wear plate is formed of a long-wearing non-ferrous material.

3. The system according to claim 2, wherein said non-ferrous material comprises a material selected from the group consisting of: ceramic impregnated ultra high molecular weight polyethylene and crosslink ultra high molecular weight polyethylene.

4. The system according to claim 1, further comprising a soil temperature sensing device mounted to the wear plate to measure soil temperature.

5. The system according to claim 1, further comprising:
    an implement for traversing a field;
    a shank with a leading edge for opening a furrow in soil as the implement traverses the field; and
    said non-ferrous wear plate being mounted to said shank behind said leading edge with said two metal prongs arranged to contact soil in a bottom of the furrow as the implement traverses the field to measure dielectric properties of the soil.

6. The system according to claim 5, further comprising a soil temperature sensing device mounted to the wear plate to measure soil temperature in the bottom of the furrow.

7. The system according to claim 1, wherein said non-ferrous wear plate is mounted on a mobile agricultural implement.

8. The system according to claim 7, wherein said mobile agricultural implement is selected from the group consisting of: planter, tillage tool, seed firmer, and irrigation pivot.

9. The system according to claim 1, further comprising:
    an implement for traversing a field;
    a shank with a leading edge for opening a furrow in soil as the implement traverses the field;
    said wear plate being mounted behind said leading edge;
    said two metal prongs being arranged to contact soil in a bottom of the furrow as the implement traverses the field to measure dielectric properties of the soil; and
    a spring-loaded mounting system for biasing said wear plate downwardly relative to said shank to maintain a consistent pressure of said wear plate and metal prongs against the soil.

10. The system according to claim 9, further comprising a printed circuit board mounted to said wear plate, and wherein said two metal prongs each have a first portion soldered directly to said printed circuit board and a second portion protruding from a bottom said of said wear plate for contacting the soil.

11. The system according to claim 10, further comprising a soil temperature sensing device mounted to the wear plate to measure soil temperature in the bottom of the furrow.

12. A system for measuring soil moisture on-the-go, comprising:
    a non-ferrous wear plate;
    two metal prongs that are supported by said wear plate, said two metal prongs isolated from each other by said wear plate and arranged to contact soil to measure dielectric properties of the soil; and
    a soil temperature sensing device mounted to the wear plate to measure soil temperature;
    wherein said soil temperature sensing device has a window through said wear plate, and said window is located between said two metal prongs.

13. A system for measuring soil moisture on-the-go, comprising:
    a non-ferrous wear plate;
    two metal prongs that are supported by said wear plate, said two metal prongs isolated from each other by said wear plate and arranged to contact soil to measure dielectric properties of the soil;
    an implement for traversing a field;
    a shank with a leading edge for opening a furrow in soil as the implement traverses the field;
    said wear plate being mounted behind said leading edge;
    said two metal prongs being arranged to contact soil in a bottom of the furrow as the implement traverses the field to measure dielectric properties of the soil; and
    a spring-loaded mounting system for biasing said wear plate downwardly relative to said shank to maintain a consistent pressure of said wear plate and metal prongs against the soil;
    wherein said spring-loaded mounting system comprises a pivot connection between a front portion of the wear plate and the lower end of the shank, and a spring arranged to bias said wear plate to rotate about said pivot connection in a direction that causes a rear portion of the wear plate to move downwardly.

* * * * *